(12) United States Patent
Mettinger

(10) Patent No.: US 6,334,445 B1
(45) Date of Patent: Jan. 1, 2002

(54) METHODS AND COMPOSITIONS FOR TREATMENT OF OVARIAN CANCER

(75) Inventor: Karl Mettinger, Miami Shores, FL (US)

(73) Assignee: Baker Norton Pharmaceuticals, Inc., Miami, FL (US)

(*) Notice: Subject to any disclaimer, the term of this patent is extended or adjusted under 35 U.S.C. 154(b) by 0 days.

(21) Appl. No.: 09/049,778

(22) Filed: Mar. 27, 1998

Related U.S. Application Data

(60) Provisional application No. 60/041,628, filed on Mar. 27, 1997.

(51) Int. Cl.[7] .............................................. A61B 19/00

(52) U.S. Cl. ..................................................... 128/898

(58) Field of Search ........................ 128/898; 435/123; 549/510; 514/449

(56) References Cited

U.S. PATENT DOCUMENTS 5,620,875 A  4/1997  Hoffman et al. ............ 435/123

OTHER PUBLICATIONS

Thigpen et al., "The role of paclitaxel in the management of coelomic epithelial carcinoma of the ovary", Semin. Oncol., 1995, 22/6 Suppl. 14 (23–31).*

Sonnichsen et al., "Clinical Pharmacokinetics of paclitaxel", Clin. Pharmacokinet., 1994, 27/4 (256–269).*

Spencer et al., "Paclitaxel A review of its pharmacodynamic and pharmacokinetic properties", Cancer Researcher Weekly, 1994, 1077–7226.*

Schiff, Peter B., et al., "Promotion of microtubule assembly in vitro by taxol", Nature, vol. 277, Feb. 22, 1979, pp. 665–667.

Schiff, Peter B., et al., "Taxol Assembles Tubulin in the Absence of Exogenous Guanosine 5'–Triphosphate or Microtubule–Associated Proteins", Biochem., vol. 20, 1981, pp. 3247–3252.

Parness, Jerome, et al., "Structure–Activity Study of Cytotoxicity and Microtubule Assembly In Vitro and Related Taxanes", Biochem. Biophys. Res. Commun., vol. 105, No. 3, 1982, pp. 1082–1089.

Weiss, Raymond B., et al., "Hypersensitivity Reactions from Taxol", J. Clin. Oncol., vol. 8, No. 7, 1990, pp. 1263–1268.

Eisenhauer, Elizabeth A., et al., "European–Canadian Randomized Trial of Paclitaxel in Relapsed Ovarian Cancer: High Dose Versus Low–Dose and Long Versus Short Infusion", J. Clin. Oncol., vol. 12, No. 12, 1994, pp. 2654–2666.

Gupta, Radhey S., "Cross–Resistance of Vinblastine–and Taxol–Resistant Mutants of Chinese Hamster Ovary Cells to Other Anticancer Drugs", Cancer Treat. Rep., vol. 69, No. 5, May, 1985, pp. 515–521.

Racker, E., et al., Use of Slow $Ca^{2+}$ Channel Blockers to Enhance Inhibition by Taxol of Growth of Drug–Sensitive and –Resistant Chinese Hamster Ovary Cells, Cancer. Treat. Rep., vol. 70, No. 2, Feb. 1986, pp. 275–278.

Schibler, Matthew J., "Taxol–dependent Mutants of Chinese Hamster Ovary Cells with Alterations in α and β–Tubulin", J. Cell Biol., vol. 201, 1986, pp. 1522–1531.

(List continued on next page.)

Primary Examiner—Dinh X. Nguyen

(57) ABSTRACT

Compositions and methods are provided which are effective in treating ovarian cancer. These compositions are easily administered by long term infusion schedules of at least 72 hours, and can be given in dosages that are safe and provide for manageable side effects. These methods and compositions for treating ovarian cancer in patients whose tumors progressed or failed to respond during prior taxane treatment of shorter duration. Surprisingly, it has been shown that longer infusion periods, such as 96 hours, give substantially lower neuropathy and certain other side effects than shorter term infusions.

5 Claims, 2 Drawing Sheets

Comparison of Paclitaxel Cmax Values (3 vs. 96 hour Infusions)

OTHER PUBLICATIONS

Lai, Gi–Ming, et al., "P–Glycoprotein Expression and Schedule Dependence of Adriamycin Cytotoxicity in Human Colon Carcinoma Cell Lines", *Int. Journ. Cancer*, vol. 49, 1991, pp. 696–703.

Wilson, Wyndham H., et al., "Paclitaxel in Doxorubicin –Refractory or Mitoxantrone–Refractory Breast Cancer: A Phase I/II Trial of 96–Hour Infusion", *J. Clin. Oncol.*, vol. 12, No. 8, 1994, pp. 1621–1629.

Hochhauser, D., et al., "Efficacy of Prolonged Paclitaxel (P) Infusion After Failure of Prior Short Taxane Infusion: A Phase II and Pharmacologic Study in Metastatic Breast Cancer (MBC)", *Br. Ca. Res. and Trt*. 1994, 32:34.

Lund, et al., "Gemcitabine in Cisplatin–Resistant Ovarian Cancer," *Semin. Oncol.*, 23(5, Suppl 10), pp. 72–76 (1996), [*Chemical Abstracts*, vol. 125, No. 25, p. 77, Col. 1, Abstract No. 125:316539 Dec. 16, 1996].

* cited by examiner

METHODS AND COMPOSITIONS FOR TREATMENT OF OVARIAN CANCER

CROSS-REFERENCE TO RELATED APPLICATIONS

This application claims priority to U.S. Provisional Application No. 60/041,628, filed Mar. 27, 1997.

TECHNICAL FIELD

The present invention relates to methods and compositions for treating ovarian cancer in humans. More particularly, the present invention relates to methods for treating ovarian cancer using a taxane composition.

BACKGROUND OF THE INVENTION

Ovarian cancer is the fourth most frequent cause of cancer death in females and in the United States, accounts for approximately 13,000 deaths annually. Moreover, the incidence is rising in industrialized countries. The etiology of the neoplastic transformation remains unknown although there is epidemiological evidence for an association with disordered endocrine function. The incidence of ovarian carcinoma is higher in nulliparous females and in those with early menopause.

Chemotherapy remains the major treatment for patients with advanced ovarian cancer. Alkylating agents induce a response in 33–65% of patients. Such alkylating agents include, but are not limited to chlorambucil, thio-tepa, and cyclophosphamide. Other agents are also known to be effective. Of these, cisplatin and carboplatin are considered to be the single most active cytotoxic agents and the response rate appears to be related to dose. A recent meta-analysis involving most of the major chemotherapy clinical trials of the 1980s in patients with ovarian cancer concluded that platinum-based therapies were the single most effective agents. It was also found that these platinum-based therapies were more effective when given in combination with another agent than when given alone. Cisplatin was also the first cytotoxic agent to demonstrate usefulness as second-line therapy, i.e., treatment for patient whose tumor had relapsed following first-line treatment with alkylating agent therapy.

In the late 1980s, several clinical studies were performed which led to the availability and use of paclitaxel in patients with ovarian cancer. Paclitaxel is now approved for use as a second-line treatment in many countries and is being evaluated as a component of front-line therapy in combination with cisplatin.

Paclitaxel is a novel microtubule stabilizing antitumor agent, originally isolated from the stem bark of *Taxus brevifolia*, the western (Pacific) yew tree. Paclitaxel acts by promoting the formation of unusually stable microtubules, and inhibits the normal dynamic reorganization of the microtubule network required for mitosis and cell proliferation. (See Schiff, P. B., et al (1979) *Nature* 277,665; Schiff, P. B., et al (1981) *Biochemistry* 20, 3247). In the presence of paclitaxel, the concentration of tubulin required for polymerization is significantly lowered. Microtubule assembly occurs without GTP and at low temperatures, and the microtubules formed are more stable to depolymerization by dilution, calcium, cold, and inhibitory drugs. Paclitaxel reversibly binds to polymerized tubulin, and other tubulin-binding drugs will bind to tubulin in the presence of paclitaxel.

Paclitaxel interacts with the microtubule system of many types of organisms. For example, in mammalian cells a 50 nM paclitaxel concentration usually causes a significant increase in microtubule number, with changes in cell shape and mitotic arrest in actively dividing cells. (Parness, J., et al. (1982) *Biochem. Biophys. Res. Commun.* 105, 1082). These perturbations of microtubule function caused by paclitaxel have a critical impact on the cell because of the role played by microtubules in cell motility, secretion, and cell division.

Paclitaxel has been studied for its effect in combating tumor growth in several clinical trials using a variety of administration schedules. Severe allergic reactions have been observed following administration of paclitaxel. However, it has been demonstrated that the incidence and severity of allergic reactions is affected by the rate of paclitaxel infusion (Weiss, R B., et al (1990) *J. Clin. Oncol.* 8, 1263).

In a study of Taxol®, (trademarked paclitaxel product of Bristol Meyers Squibb), in over 400 patients with ovarian cancer, patients were randomized two ways, (1) between 135 to 175 mg/m$^2$ and (2) between 3-hour and 24-hour infusions. In this study, minor degrees of flushing were seen in 42% but severe hypersensitivity reactions were seen in only 1–2% without influence of dose or schedule on frequency or severity. Neurosensory symptoms, described as burning paresthesia, occurred more frequently (52%) at the 175 mg/m$^2$ dose as compared with 36% at the lower dose. A syndrome of arthralgia, with onset 1–2 days after administration and lasting a few days, was common (55–65%) and more frequent at the higher dose.

Myelosuppression (primarily granulocytopenia) occurred frequently but was most common with the 24-hour infusion (71%). Only 18% of patients receiving drug by a 3-hour infusion developed Grade 4 granulocytopenia. Febrile neutropenia was documented only with the 24-hour infusion. Stomatitis occurred in 22–30% of the patients and was severe in less than 2% of the patients. Cardiovascular effects were rare. Asymptomatic bradycardia (pulse<50 beats/min.) was observed in only 1% of cycles (26 of 2354 cycles) and hypotension (systolic <80 mm Hg) in only 13 of 2354 cycles. Nine patients discontinued Taxol® treatment because of nonhematologic toxicity. Of these patients, 4 had neurotoxicity, 3 had hypersensitivity, 1 had mucositis and 1 had idiopathic pulmonary edema.

Infusion times, from 3 hours up to 24 hours, have been used in treatment with paclitaxel to decrease the incidence of toxicity and side effects, including allergic reactions to the drug. Data from these studies indicate that reversible myelosuppression is the dose limiting toxicity, with significant peripheral neuropathy observed at doses of 275 mg/m$^2$ and greater. Other toxicities include myalgia, mucositis, and alopecia.

Paclitaxel was approved by the FDA in December 1992, for treatment of ovarian cancer after failure of first-line or subsequent chemotherapy. This approval was based on the initial Phase II studies and on the National Cancer Institute compassionate plea program, where paclitaxel was administered over a 24-hour period. More recently, the more convenient 3-hour schedule has been approved for the same indication in many countries.

Studies of paclitaxel in breast cancer treatment has been reported. In single agent studies, response rates have been found to be dose related, with a 13–37% response rate for doses of 135 to 175 mg/m$^2$, compared to a 36–71% response rate for doses of 250 mg/m$^2$ with G-CSF. The highest response rate (79%) has been reported in a 600 patient study using paclitaxel (135 mg/m$^2$) in combination with cisplatin (75 mg/m$^2$).

In a European-Canadian multi-institutional trial with ovarian cancer patients, 407 patients were randomized to one of two dose levels (135 mg/m$^2$ or 175 mg/m$^2$), given every three weeks, and to either a 3-hour or 24-hour schedule. See Eisenhauer, E.A. et al "European-Canadian randomized trial of paclitaxel in relapsed ovarian cancer: High dose versus low-dose and long-term versus short infusion." *J. Clin. Onc.* 1994. 12:2654–66. The response rate was higher at the 175 mglm$^2$ dose (20%) than the 135 mg/m$^2$ dose (15%) but the difference was not statistically significant. Time to tumor progression was significantly longer (19 weeks vs 14 weeks) in patients receiving the higher dose. Overall survival based on deaths in about 25% of patients were similar in the different subsets. Thus, the study concluded that the shorter (3-hour) infusion was nearly as efficacious, yet safer and more convenient than the 24-hour infusion.

Paclitaxel, like other chemotherapy agents, has been shown to create drug resistance in tumor cells. Drug resistance by tumor cells is a common response to chemotherapy agents. Two mechanisms of paclitaxel resistance have been identified in vitro. In one cell type, resistance is due to drug efflux, which is the result of increased levels of membrane P-glycoproteins causing increased drug efflux. (Gupta, R. S. (1985) *Cancer Treat. Rep.* 69, 515). These cells are also resistant to the vinca alkaloids, doxorubicin, and other natural products, and resistance is reversible with calcium channel blockers such as verapamil (Racker, E., et al (1986) *Cancer Treat. Rep.* 70, 275). Another mechanism of resistance found in other paclitaxel resistant cells involves mutations in the alpha- or beta-tubulin subunits. (Schibler, M. J., et al (1986) *J. Cell Biol.* 102, 1522).

Experimental evidence suggests that the cytotoxicity of paclitaxel is both schedule-dependent and highly dependent on exposure time. Thus both anti-tumor effect and myelosuppression might be expected to be greater with longer infusions. Longer drug exposure times with some natural agents, including paclitaxel, may also partially overcome multidrug resistance (mdr) associated with the mdr-1 gene. Drug resistance MCF 7 cells were 4.4 fold less resistant to a 24-hour continuous exposure to paclitaxel than to a 3-hour exposure. See Lai, G.M. et al "P-glycoprotein expression and schedule dependence of adriamycin cytotoxicity in human colon carcinoma cell lines." *Int. J. Cancer* (1991) 49:696–703. Based on this in vitro data, a Phase I/II trial of a 96-hour schedule was completed in doxorubicin or mitoxantrone-refractory breast cancer patients. See Wilson, W. H. et al. "Paclitaxel in doxorubicin-refractory or mitoxantrone-refractory breast cancer: A phase I/II trial of 96-hour infusion." *J. Clin. Oncol.* (1994) 12:1621–1629. In the Phase II part of the study, breast cancer patient received a dose of 140 mg/m$^2$ taxol (BMS, Bristol Meyers Squibb) over a 96-hour period. A partial response was observed in 16 of 33 patients (48%) and a minor response was observed in 5 (15%). Another report of breast cancer treatment indicated that a 96 hour infusion schedule of taxol (BMS) may be efficacious for breast cancer treatment. See Hochhauser, D. et al, "Efficacy of prolonged paclitaxel infusion after failure of prior short taxane infusion: A phase II and phamacologic study in metastatic breast cancer. *Br. Ca. Res. and Trt.* (1994) 32:34. These investigators administered taxol (BMS) via a 96-hour infusion at a total dose of 140 mg/m$^2$ to 25 patients with measurable metastatic breast cancer, in each of whom tumor had progressed during a prior course of either taxol (BMS) by 3 hour infusion or taxotere by 1-hour infusion. 28% of the patients achieved an objective tumor response despite prior clinical evidence of taxane resistance.

What is needed are methods and compositions for treating patients with ovarian cancer. Particularly what is needed are methods and compositions for patients with ovarian cancer who have had tumor progression after treatment with short term infusion schedules of taxanes. Furthermore, no one has been able to demonstrate an effective regimen for treatment of ovarian cancer that overcomes the problem of multi-drug resistance.

Thus, methods and compositions are needed that are capable of treating ovarian cancer that is refractory to short term infusion schedules of taxanes, such as taxotere or paclitaxel. Moreover, an infusion treatment regimen that would be efficacious in treatment of multi-drug resistance ovarian cancer would be beneficial. Additionally, methods and compositions that are easily administered are necessary. In addition to infusion methods, a simple and efficacious method of treatment would be through the oral route.

What is also needed are methods and compositions for treating patients with ovarian cancer who have had tumor progression after treatment with known chemotherapy agents such as platinum-based chemotherapy treatments. What is particularly needed are compositions and methods for treatment of patients with ovarian cancer who have tumor progression after systemic treatment with known chemotherapy agents such as platinum-based chemotherapy treatments and who are refractory to short term infusion (1 to 24 hour) of taxane therapy.

Thus, methods and compositions are needed that are capable of treating ovarian cancer that is refractory to known chemotherapy agents and short term infusion schedules of paclitaxel. Moreover, an infusion treatment regimen that would be efficacious in treatment of multi-drug resistance ovarian cancer would be beneficial. Additionally, methods and compositions that are easily administered are necessary. A simple and efficacious method of treatment would be through the oral route, particularly if the oral administration provides pharmacokinetic benefits similar the pharmacokinetics of the 96-hour infusion of paclitaxel.

SUMMARY OF THE INVENTION

In accordance with the present invention, compositions and methods are provided that are effective in treating ovarian cancer. These compositions are easily administered by long term infusion schedules of at least 72 hours, and can be given in dosages that are safe and provide for manageable side effects. The present invention provides methods and compositions for treating ovarian cancer in patients whose tumors progressed or failed to respond during prior taxane treatment of shorter duration and also treatment of patients who have previously undergone known chemotherapy treatment, such as treatment with platinum-based chemotherapy, and who are refractory to short-term taxane treatment. Surprisingly, it has been shown with the present invention that longer infusion periods, such as 96 hours, give substantially lower neuropathy and certain other side effects than shorter term infusions. Thus, the longer-infusion periods contemplated in the present invention obviate the need for premedications that other paclitaxel treatments require.

The present invention comprises methods and compositions for treating ovarian cancer with a long term exposure to paclitaxel. Such a schedule includes infusion times on the order of at least 72 hours, more preferably at least 96 hours. Such long term infusion schedules may enhance the activity of drugs, such as paclitaxel, which are transported by P-glycoprotein. Thus a preferred embodiment of the present invention is to administer paclitaxel as a 96 hour infusion treatment in patients with ovarian cancer, to effectively treat the ovarian cancer and to reduce the chances of developing mdr (multidrug resistance) paclitaxel resistance.

The present invention also includes ovarian cancer treatment compositions that contain paclitaxel. These ovarian cancer treatment compositions can be administered to humans with ovarian cancer at doses of 70 mg/m² to 200 mg/m², more preferably at doses of 100 mg/m² to 175 mg/m², most preferably 140 mg/m², the dose level being dependent on the toxicity of paclitaxel to the patient.

Accordingly, it is an object of the present invention to provide methods and compositions to treat ovarian cancer.

It is yet another object of the present invention to provide methods of treatment of ovarian cancer comprising long term infusion schedules.

It is another object of the present invention to provide methods of treatment for patients with ovarian cancer that have had tumor progression after treatment with other chemotherapy regimens.

Another object of the present invention is to provide compositions comprising taxanes for the treatment of ovarian cancer.

It is yet another object of the present invention to provide a treatment for patients with ovarian cancer who were refractory to treatment with short term infusion treatment with taxanes.

A further object of the present invention is to provide methods and compositions for a treatment of ovarian carcinoma in patients who have undergone at least one prior chemotherapy regimen, including but not limited to platinum based therapies or taxane therapies, and who has had tumor progression.

It is another object of the present invention to provide methods and compositions of paclitaxel treatment that reduce or eliminate the development of mdr paclitaxel resistance.

It is another object of the present invention to provide methods and compositions of paclitaxel treatment that reduce or eliminate the need for premedication of the patients.

These and other objects, features and advantages of the present invention will become apparent after a review of the following detailed description of the disclosed embodiments and the appended claims.

Detailed Description

Figure 1:
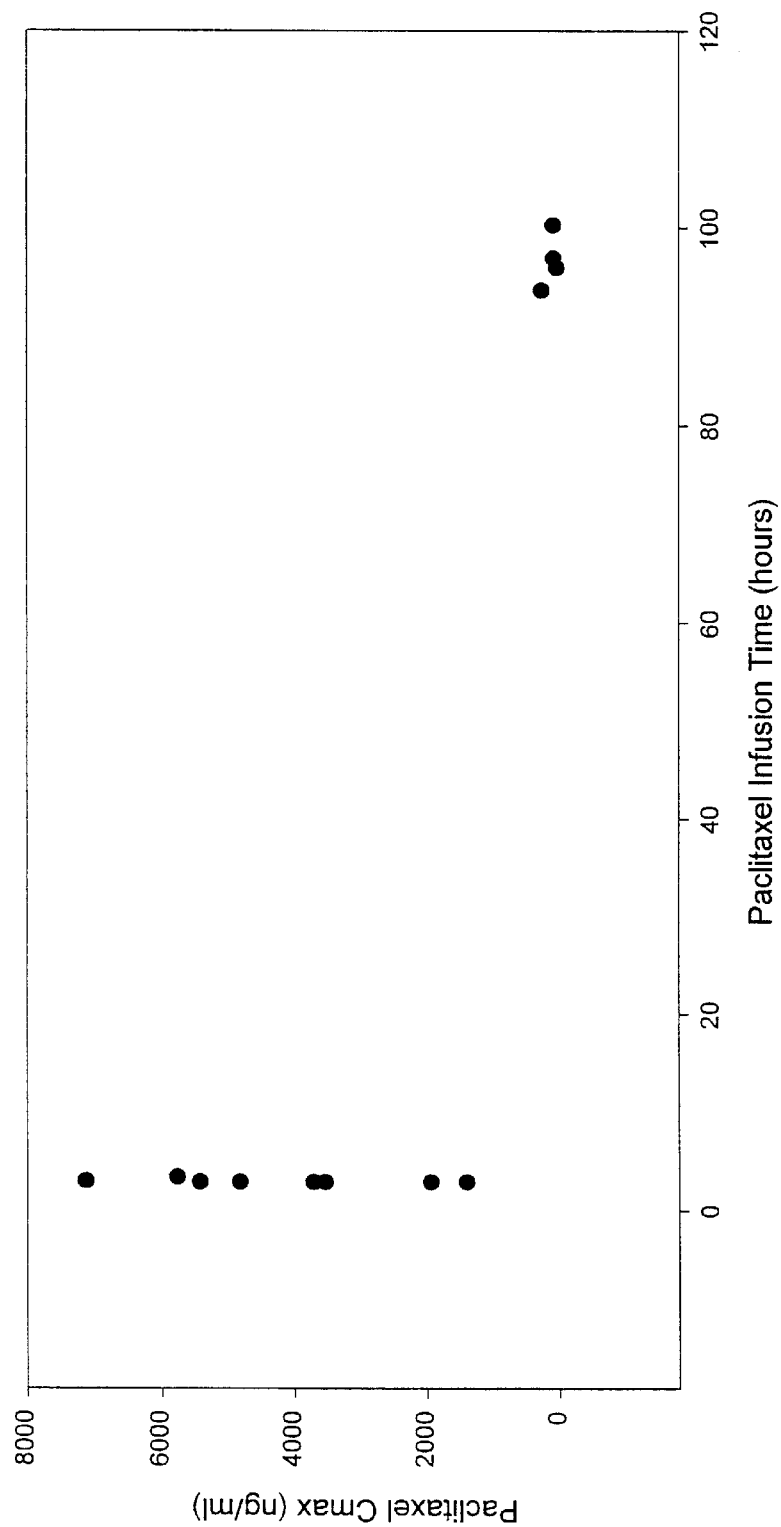
FIG. 1 is a comparison of paclitaxel Cmax values.
Figure 2:
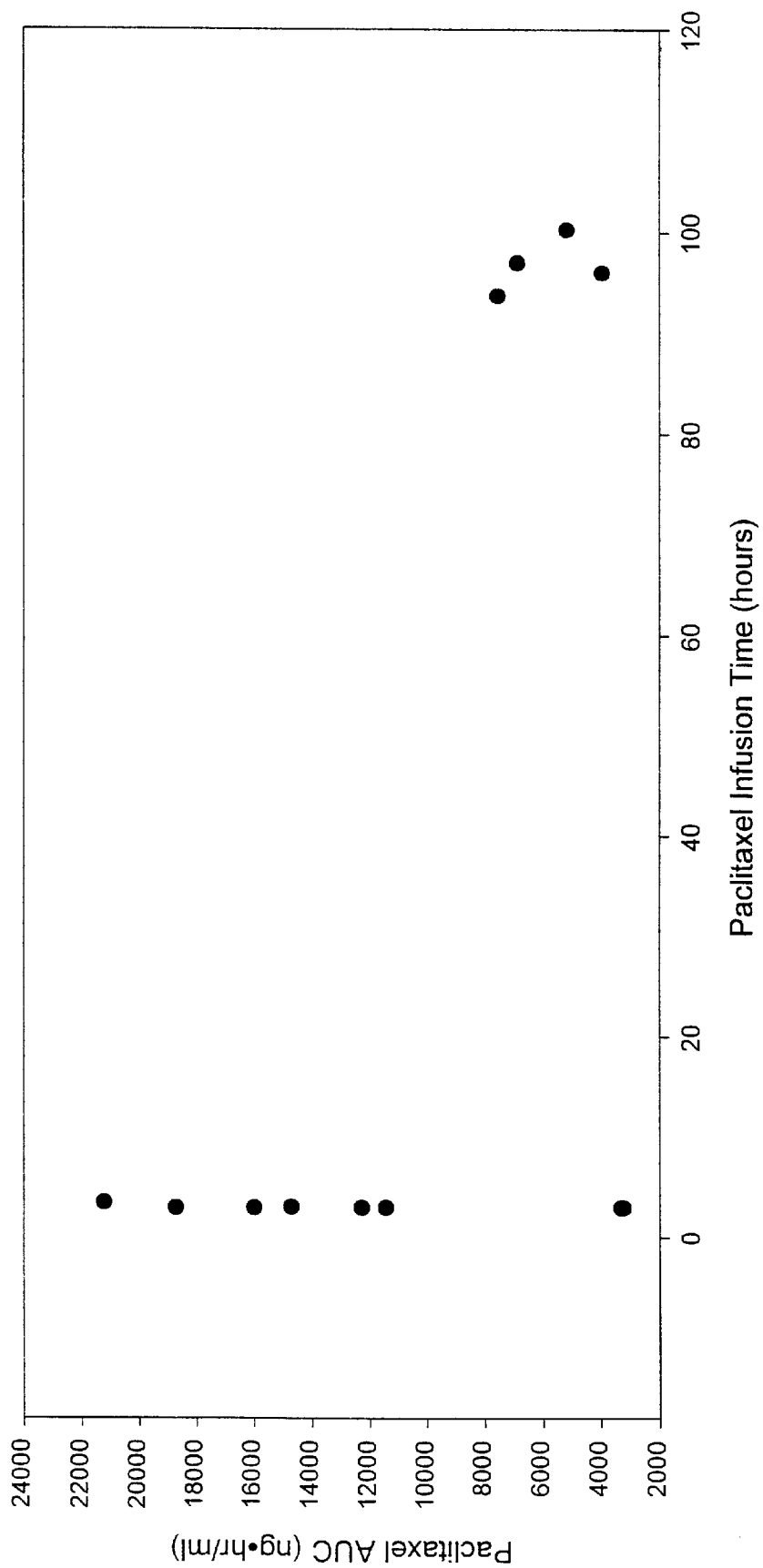
FIG. 2 is a comparison of paclitaxel AUC values.

The present invention comprises compositions and methods for the treatment of ovarian cancer. One embodiment of the present invention is the use of taxanes, such as paclitaxel or taxotere, via long term infusion schedules to treat refractory ovarian cancer. Treatment of patients with the present invention causes substantially lower neuropathy and certain other side effects in the patients than shorter term infusions. Thus, the longer infusion periods contemplated in the present invention obviate the need for premedications that short term infusion paclitaxel treatments require.

The present invention also comprises treatment of patients with advanced ovarian carcinoma who have failed taxane treatments with infusions of shorter duration such as 1 to 24 hours. As used herein, taxane treatment includes treatment with paclitaxel, taxol (BMS), taxotere and other related compounds.

Preferred embodiments of the present invention include the treatment of patients with ovarian cancer (advanced ovarian carcinoma) at dosages of a taxane at 70 mg/m² to 200 mglm², more preferably at doses of 100 mg/m² to 175 mg/m², most preferably 140 mg/m², the dose level being dependent on the toxicity of paclitaxel on the patient. The infusion schedule for such methods include duration of at least 72 hours, more preferably 96 hours. Compositions in the present invention include taxanes, preferably paclitaxel or taxotere, most preferably paclitaxel. In a most preferred embodiment, the present invention includes methods of treatment of patients with ovarian cancer who are treated at a 96 hour infusion rate with a dose of 140 mg/m²;paclitaxel every 21 days.

As used herein, paclitaxel (USAN generic name) is 5β, 20-epoxy-1 ,2α4,7β10β13α-hexahydroxytax-11-en-9-one 4, 10-diacetate 2-benzoate 12-ester with (2R,3S)-Nbenzoyl-3-phenylisososerine.

The patients to be treated by the present invention include humans with ovarian cancer. In one embodiment of the present invention, the methods and compositions are useful for patients who have previously undergone taxane treatment with infusion rates of 1–24 hours. It is also envisioned by the present invention that patients who have ovarian cancer, who have undergone systemic chemotherapy, such as platinum-based therapies, including cisplatin and carboplatin, would be treated with the methods and compositions of the present invention. Furthermore, it is also envisioned that the present invention has utility for treatment of ovarian cancer in patients who have undergone systemic chemotherapy treatments and short term duration taxane infusion and who have had tumor progression.

For example, the following description teaches the administration of a composition comprising paclitaxel. Use of other taxanes in place of the paclitaxel of the example is considered part of the present invention. Use of other medical devices such as containers and infusion equipment are also contemplated by the present invention.

Paclitaxel BNP (Baker Norton Pharmaceutical) is supplied as a concentrated sterile solution, 6 mg/mL in 5 ampoules (30 mg/ampoule). Each mL of sterile solution contains 527 mg polyoxyethylated castor oil (Cremophor® EL) and 49.7% (w/v) absolute alcohol BP. The contents of the ampoules must be diluted prior to clinical use. The unused portions of any opened ampoules should be disposed of using OSHA approved guidelines.

Vials should be stored either in room temperature (approximately 25° C.) or under refrigeration (2–8° C.). Each infusion-ready paclitaxel solution (paclitaxel infusion solution) should be administered within 24 hours after preparation. Paclitaxel infusion solutions may exhibit a slight haziness directly proportional to the concentration of drug and time elapsed after preparation. When prepared, paclitaxel infusion solutions (0.3–1.2 mg/mL paclitaxel) are stable at ambient temperature (approximately 25° C.) and normal lighting conditions for up to 48 hours. Formulation of a small number of fibers in the paclitaxel infusion solution (within acceptable limits established by the USP Particulate Matter Test for LVP's) has been observed after preparation of paclitaxel infusion solutions. While particulate formation does not indicate loss of drug potency, solutions exhibiting excessive particulate matter formation should not be used. In-line filtration may be necessary and can be accomplished by incorporating a hydrophilic, microporous filter with a pore size no greater than 0.22 microns (IVEX-HP In Line Filter Set-SL, 15", Abbott model #4525 or equivalent) into the fluid pathway distal to the infusion pump.

Paclitaxel must be prepared in nonplasticized solution containers (e.g., glass, polyolefin, or polypropylene) due to leaching of diethylhexylphthlalate (DEHP) plasticizer from polyvinyl chloride (PVC) bags and intravenous tubing. Paclitaxel must not be administered through PVC intravenous sets. Therefore, polyolefin-line or polyethylene-line sets, such as (IV) nitroglycerin sets (or equivalent) should be used to connect the container of the paclitaxel infusion solution to the IV pump, a 0.22 micron filter is then attached to the IV set, and then may be directly attached to the patient's central access device. If necessary, a polyolefinline extension set (Polyfin™-Extension Set, MiniMed technologies, Model #126) can be used to provide additional distance between the IV pump and the patient's central access device.

To practice the invention, the final paclitaxel infusion solution may be prepared by diluting the total daily paclitaxel dose (i.e., a 24 hour supply) in 250 or 500 mL of 5% Dextrose Injection, USP or 0.996 Sodium Chloride Injection, USP in either a glass, polyolefin or polypropylene container. Each paclitaxel infusion solution will be infused over 24 hours via an infusion control device. A total of four paclitaxel infusion solutions are required for each 96 hour infusion. Each paclitaxel infusion solution should be prepared immediately prior to use such that no more than 25 hours will elapse from the time of preparation until the end of the infusion for each bag/bottle. A polyolefin- or polyethylene-line set should be used to connect the bag/bottle to the IV pump, followed by the in-line filter which will be directly attached to the patients central access device.

An embodiment of the present invention involves administration of a paclitaxel infusion solution as a 96 hour continuous intravenous infusion. The paclitaxel infusion solution is delivered through a permanent central intravenous catheter, with cycles repeated every 21 days. It is preferred that patients have a permanent or temporary central venous access for ease of administration. Alternatively, oral administration of taxanes that provide pharmacokinetic benefit similar to that of the 96 hour infusion treatment could be administered without requiring the patient to have a central venous access.

A preferred embodiment of the present invention is a method of treatment of patients with ovarian cancer who have had disease progression after prior treatment. Such prior treatment can include, but is not limited to short duration infusion of taxanes, platinum-based therapies such as carboplatin or cisplatin, or other systemic chemotherapy treatment. A most preferred embodiment of the present invention is a method of treatment of humans with ovarian cancer who have had disease progression after short duration (1–24 hour) infusion treatment with paclitaxel.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

Women with measurable ovarian cancer whose tumor progressed or failed to respond during prior taxane treatment given by shorter duration (1–24 hours) infusion were enrolled in a study. Patients were evaluable if they completed at least two cycles of paclitaxel BNP. Patients with taxane-resistant ovarian cancer are defined as having (1) progression of disease while receiving taxane therapy; (2) progression within 12 months of taxane therapy; (3) persistent stable disease after six courses of taxane therapy; or (4) persistent stable disease with at least CA-125 rising measurements (to a value of $\geqq 100$).

With the 96 hour infusion treatment plan, no antihypersensitivity premedication was required. Surprisingly, it has been shown with the present invention that longer infusion periods, such as 96 hours, give substantially lower neuropathy and certain other side effects than shorter term infusions. Thus, the longer infusion periods contemplated in the present invention obviate the need for premedications that other paclitaxel treatments require. Patients without liver function abnormalities (normal alkaline phosphatase, bilirubin, SGOT) or without liver metastases, received paclitaxel BNP at a dose of 35 mg/m$^2$/day ×4 days (total dose of 140 mg/m$^2$ over 96 hour infusion). Patients without liver metastases and who had mild liver function abnormalities (SGOT and alkaline phosphatase less than 1.5 times upper normal limit) and a normal bilirubin received a total dose of 140 mg/m$^2$. Patients with moderate and severe liver function abnormalities (SGOT and alkaline phosphatase greater than 1.5 times upper normal limit) received paclitaxel BNP at a dose of 26.25 mg/m$^2$/day (total dose of 105 mg/m$^2$ over 96-hour infusion).

Cycles of paclitaxel BNP were repeated every 21 days. Such treatment schedule was followed provided that recovery of hematologic and all other toxicities (except alopecia) had returned to Grade 1.

Paclitaxel BNP was obtained as a concentrated solution, 6 mg/niL, in 5 mL vials (30 mg/vial). Each mL of sterile solution contains 527 mg polyoxyethylated castor oil (Cremaphor® EL) and 49.7% (w/v) absolute alcohol. The paclitaxel was then diluted in 500 mL 5% Dextrose, to a concentration sufficient to supply 35 mg of paclitaxel per square meter (based on the body surface area of the patient) over a 24 hour period. The paclitaxel infusion solution was prepared between 30 and 60 minutes prior to beginning each 24 hour infusion. The paclitaxel infusion solution was prepared in a polypropylene lined semi-rigid container, in a volume of 500 mL.

The container with the paclitaxel infusion solution was connected to an IV pump via a polyethylene tube, an IVEX-HP In Line Filter Set-SL, 15", Abbott model #4525 with a pore size of 0.22 microns was then attached to the IV pump via a polyethylene line-tubing. The in-line filter was then connected to the subjects central access device.

The paclitaxel solution was infused over a 24 hour period, and was controlled by the infusion device. The procedure was repeated three more times, for a total 96 hour continuous infusion. The final dose was 140 mg/m$^2$/96 hours.

The following criteria were used to measure the response to the above described paclitaxel treatment:

Complete response (CR): Complete disappearance of all clinical evidence of disease persisting through the next evaluation period at 6 weeks. Evaluable lesions must have disappeared completely.

Partial Response (PR): At least 50% decrease in the sum of the products of the diameters of all measurable lesions persisting through the next evaluation period at six weeks. In addition, concomitant evaluable lesions must show no evidence of progressive disease or new lesions.

Stable Disease (SD): Patients who do not qualify for response nor progressive disease.

Progressive Disease (PD): 25% or greater progression in the sum of the products of the diameter of any measurable lesion(s) over one cycle of chemotherapy or the appearance of any new lesion consistent with metastatic disease.

14 patients with ovarian carcinoma who had been treated previously with shorter duration taxane treatment and yet still had disease progression, underwent the 96 hour paclitaxel infusion treatment described above. Of those 14, 3 had partial responses, giving a 21% response rate. One patient had stable disease. Thus, the overall response rate was 29%.

It should be understood, of course, that the foregoing relates only to preferred embodiments of the present invention and that numerous modifications or alterations may be made therein without departing from the spirit and the scope of the invention as set forth in the appended claims.

What is claimed is:

1. A method of treating ovarian cancer in a human having ovarian cancer, comprising the step of intravenously infusing a composition comprising a taxane into the human at continuous dosage over a period of 96 hours, wherein the human had previously undergone taxane treatment of 1–24 hour infusion unsuccessfully.

2. The method of claim 1, wherein the taxane is paclitaxel.

3. The method of claim 1, wherein the continuous dosage comprises 100 to 140 mg/m$^2$ per 96 hours.

4. The method of claim 1, wherein the human had also undergone platinum-based chemotherapy unsuccessfully.

5. The method of claim 1, wherein the step of intravenously infusing is repeated every 21 days.

* * * * *